(12) United States Patent
Hernandez-Ramirez et al.

(10) Patent No.: US 8,309,103 B2
(45) Date of Patent: Nov. 13, 2012

(54) ASSOCIATION OF FLUCONAZOLE-TINIDAZOLE FOR THE TREATMENT OF VAGINAL INFECTIONS, ITS COMPOSITION, PREPARATION PROCESS AND USAGE

(75) Inventors: Luisa Hernandez-Ramirez, Edo. de Mexico (MX); Angelica Arzola-Paniagua, Col. San Jeronimo Lidice (MX); Raul E. Garcia-Salgado-Lopez, Edo. de Mexico (MX); Fernando Poot-Lopez, Mexico (MX)

(73) Assignee: Alparis, S.A. DE C.V., Morales (MX)

( * ) Notice: Subject to any disclaimer, the term of this patent is extended or adjusted under 35 U.S.C. 154(b) by 1467 days.

(21) Appl. No.: 10/762,616

(22) Filed: Jan. 22, 2004

(65) Prior Publication Data

US 2005/0165077 A1   Jul. 28, 2005

(51) Int. Cl.
  *A01N 25/34*   (2006.01)
  *A61K 31/41*   (2006.01)
  *A61K 31/415*  (2006.01)
  *C07D 249/08*  (2006.01)
  *C07D 233/91*  (2006.01)

(52) U.S. Cl. ........ 424/400; 424/404; 514/383; 514/397; 548/266.6; 548/330.5

(58) Field of Classification Search .............. 514/383, 514/397; 424/404; 548/266.6, 330.5
See application file for complete search history.

(56) References Cited

U.S. PATENT DOCUMENTS

| | | | |
|---|---|---|---|
| 5,120,735 A | | 6/1992 | Arika |
| 5,536,743 A | | 7/1996 | Borgman |
| 5,660,860 A | * | 8/1997 | Fielden ........................ 424/464 |
| 5,840,744 A | | 11/1998 | Borgman |
| 5,980,882 A | * | 11/1999 | Eichman .................... 424/78.12 |
| 6,416,779 B1 | | 7/2002 | D'Augustine |
| 6,440,949 B1 | | 8/2002 | Zeng |
| 6,706,270 B1 | | 3/2004 | Ruelle |
| 2003/0017207 A1 | | 1/2003 | Lin et al. ....................... 424/486 |
| 2003/0059471 A1 | * | 3/2003 | Compton et al. ............. 424/489 |
| 2003/0064103 A1 | | 4/2003 | Lin et al. ....................... 424/486 |
| 2003/0130225 A1 | * | 7/2003 | Ahmad et al. ................. 514/45 |
| 2003/0236236 A1 | * | 12/2003 | Chen et al. ..................... 514/171 |
| 2004/0033968 A1 | * | 2/2004 | Lin et al. ........................ 514/27 |

FOREIGN PATENT DOCUMENTS

| | | |
|---|---|---|
| MX | 188752 | 4/1998 |
| MX | 02/07641 | 4/2004 |

OTHER PUBLICATIONS

Gillis et al. (Drugs. Apr. 1996; 51(4):621-38).*
Cipla (Cipla: Therapeutic Index: Gynecological Products: Forcan TZ KIT: Fluconazole and Tinidazole: 2000).*
Malhotra et al. (Indian J of Medical Sciences (2003); 57(12):549-555).*
Videau et al. (Br. J. Vener. Dis. (1978);54;77-80).*
Wallin et al. (Br. J. Vener. Dis. (1974);50;148-150).*
Spielberg C.A. (Clin. Lab. Med.(Sep. 1989); 9(3):525-33).*
Sobel et al. (Am J Obstet Gynecol(Apr. 1995); 172(4 Pt. 1):1263-8).*
Gennaro, Alfonso. Remington's pharmaceutical Sciences. Easton, PA:Mack Pub. Co., 1990. 18th Ed.*
Gillis et al. (Drugs(Apr. 1996);51(4):621-38).*
Boedeker et al ("Fluconazole dose recommendation in urinary tract infection." Ann Pharmacother. Mar. 2001;35(3):369-72).*
*Drugs* 49 (6) pp. 984-1006, 1995, Caroline M. Perry, Ruth Whittington and Donna McTavish.
Boletin Nov. 15, 2002 *Fermscoepidemiologia*.

* cited by examiner

*Primary Examiner* — James D Anderson
*Assistant Examiner* — Chris Simmons
(74) *Attorney, Agent, or Firm* — Husch Blackwell LLP

(57) ABSTRACT

The present invention refers to a treatment for mixed infectious diseases in the human reproductive system, wherein an association of compounds containing fluconazole and either tinidazole or secnidazole is used, the same being associated in doses lower to those commonly used therapeutically. The combination has proven to be highly efficacious and shown a good degree of tolerance.

3 Claims, No Drawings

ASSOCIATION OF FLUCONAZOLE-TINIDAZOLE FOR THE TREATMENT OF VAGINAL INFECTIONS, ITS COMPOSITION, PREPARATION PROCESS AND USAGE

FIELD OF THE INVENTION

The present invention is related to the treatment of infectious diseases in the female reproductive system and more particularly to the use of an ASSOCIATION of compounds comprising fluconazole and tinidazole associated in doses lower to those usually administered therapeutically. This combination has proven to be highly effective and well tolerated.

BACKGROUND OF THE INVENTION

In medical practice vaginal infections are a common health hazard, since up to 95% of the patients go to the doctor due to vaginal flow. In primary health services, these infections affecting teenagers are found to be among the three topmost reasons for the visit, their incidence being much higher among the sexually active, although it has also been found among the girls who are not.

Normal vaginal secretions are inodorous, clear, viscous, with a Ph below 4.5, contain no necrophilia and do not flow during an examination with a speculum.

Among the factors favorable to vaginal infections we have poor genital-anal hygiene, a new sex partner or several of them, bathing in pools or tubs, pregnancy, diabetes, parasitic infections, urinary or fecal incontinence, stress, congenital malformation, frequent use of antibiotics, hormones, contraceptive preparations to be used orally or topically and vaginal, immune system deficiency, tight clothes, nylon underwear, using non-hygienic vaginal elements used for the application of products and so forth.

The most frequent vaginal infections are shown in the table below.

| Clinical Framework | Etiological Agent |
|---|---|
| Scarce whitish flow, pH < 4.5<br>Vulva itch and/or<br>irritation, erythema,<br>profuse yellow flow, pH > 5 | Candida albicans<br>Trichomonas vaginallis |
| Vulva itch, malodorous<br>white-grayish flow, pH > 4.5<br>A smell of amines | Gadnerella vaginallis<br>(Haemophilus vaginallis)<br>Anaerobes<br>(peptostreptococcus<br>bacteria, porphyromons)<br>after the addition of<br>potassium hydroxide<br>Mobiluncus spp |
| 10%* presence of guide cells | Mycoplasma hominis<br>(Amsel's Criteria) |
| Abnormal flow, post-coital bleeding | Chlamidia trachomatis |

Vaginal infection or vaginal flow syndrome is an infectious process characterized by one or more of the following symptoms: flow, vulva itch, burning, irritation, dysuria, dyspareunia and vaginal malodor; a microorganism is often to be found during vaginal infection, which originates mixed vaginal infections.

Vulvovaginitis, vulvitis and vaginitis are terms usually related to a swelling of the vagina or vulva, frequently caused by fungi, bacteria and parasites. By vulvovaginitis we understand the anomalous and irritating flow of secretion, whether malodorous or not, which produces local discomfort (itching or burning sensation) and which can be accompanied by dysuria and/or dyspareunia. Vulvovaginitis is the most frequent gynecological problem leading to a first visit to the doctor. 90% of females showing symptoms suffer from a bacteria sort of infection (mostly Gardnerellas), candidiasis or Trichomonas. The remaining 10% show a different set of symptoms: ETS, vaginal atrophy, allergies and chemically induced irritation. Candidiasic vulvovaginitis (VVC) is the most common cause of vaginitis in Europe. About 85-90% of the cases are due to Candida Albicans. The initial treatment makes use of topical agents.

Initial treatment make use of topical agents such as creams, vaginal tablets, and ovules for periods from 7 to 10 days, with the ovules and creams a recovery rate of no more than 75% percent is achieved. Due to the high level of discomfort for the patient, presence of adverse reactions or drug interactions, and the length of the treatment, other options for the treatment of vaginal infections have been sought, such as the use of systemic treatments and even the shortening of the period of the treatment itself. Some treatments may include the use of clotrimazole, miconazole, fenticonazole and nistatine. In the case of severe infections, recurrent ones or intolerance to vaginal application, the use of 400 mg a day of ketoconazole for 5 days or 200 mg of itraconazolere for 3 days or 400 mg 400 mg one day or 150 mg of fluconazole for one day is recommended. Drugs 49(6) 984-1006, 1995.

In the case of highly severe or chronic infections (4 or more episodes a year) an oral treatment is used and, to avoid a recurrence, 100 mg of ketoconazole a day is used during 6 months, a vaginal ovule of cotrimazol a month in the premenstrual stage during 6 months, or 200 mg of Itraconazole taken orally for 3 days during 6 cycles. Boletín 15 de Nov. 2002 Farmacoepidemiología Bacteria induced vaginitis represents an alteration of the vaginal flora characterized by a decrease in the concentration of hydrogen peroxide produced by the lactobacilli and an increase in the prevalence of Garnerella vaginalis, and negative gram anaerobes which bring about the onset of malodorous flow without showing any signs of vulvo vaginal swelling. In bacteria induced vaginitis most of the lactobacilli disappear, vaginal pH increases and a pathogenic proliferation of other anaerobes bacteria is found. There are four bacteria associated to bacteria induced vaginitis: Gardenerella vaginalis, a facultative, fermentative anaerobes present in 40% of the average female, and the most commonly associated to this pathological condition (95%); Mobiluncus, Mycoplasma hominis as examples of negative gram anaerobes, and Peptostreptococcus. By oral via the preferred treatment is metronidazole: 50 mg taken orally, every 12 hours for 7 days. As alternative paths 2 g of metronidazole in an only dose or 300 mg of Clindamycin taken orally twice a day for a week are used.

Vulvovaginitis due to Trichomona is a process caused by mobile protozoa, flagellate and anaerobic called Trichomonas vaginalis and is acquired due to sexual intercourse. It is one of the main causes of vaginal infections. Fifty per cent of the patients (both male and female) are non symptomatic at the moment of the diagnoses. A third of them will develop the symptoms in the following 6 months if not treated. The most recommended pattern for the treatment is to take 2 grams of metronidazole in an only dose, whether male or female. By means of this therapeutic regime, and if also the sexual partner is involved, up to 85% of efficacy can be reached.

Taking into account that in the same woman several clinical variations may coexist and that the presence of a particular form of etiological agent cannot be fully determined by a gynecologic exam, the treatment should be approached as syndromes; concentrating on the most common infections associated to the vaginal flow syndrome: trichomoniasis, candidiasis and bacterial vaginosis as in those cases the infection is mixed.

The following table shows a resume of the most commonly prescribed treatments:

TABLE 1

| Candidiasis | Trichomoniasis |
| --- | --- |
| Isoconazole, 1%, vaginal cream, 7 to 14 days. | Metronidazole, 250 mg, orally, 3 × day, 7 days |
| Miconazole, cream or ovules, 7 days | Metronidazole, 2.0 g, orally, one dose |
| Tioconazole 6.5%, topical, one dose | Tinidazole, 2.0 g oral, one dose |
| Terconazole, cream at 0.8%, 7 days | Secnidazole 2.0 g, oral, one dose |
| Fluconazole 150 g oral, one day | Miconazole + Tinidazole associated, vaginal cream, 7 days |
| Itraconazole 400 mg-1 day or 200 mg, 3 days | |
| Ketoconazole 200 mg, 2 tablets, oral, 5 days | |

| Gardnerella | Neisseria/Clamydia |
| --- | --- |
| Metronidazole, 500 mg. oral, twice a day, 7 days | Ceftriaxone 250 mg, IM one dose |
| Tinidazole 2.0 g, oral, one dose | Azithromycin 1.0 oral, one dose |
| Clindamycin 30 mg oral, 2 a day, 7 days | Doxocilin 100 mg oral, 2 a day, 7 days |
| Clindamycin 2% vaginal cream 3 to 7 days | Ofloxacin 300 mg oral 2 a day, 7 days |
| | Eritromicin stearate 500 mg oral 4 times a day, 7 days |

In the state of the art there are several published works where reducing the length of the treatment is being sought.

The U.S. Pat. Nos. 6,416,779, 5,120,735, 6,706,270, 6,440,949 and 5,840,744 show different treatments, methods and compositions for intravaginal or transvaginal delivery, doses of a pharmaceutical agent to the vagina, nevertheless, it is important to be considered that the vaginal application may not be well accepted by the patient.

It is renown that the active agents with pharmaceutical qualities that have been developed or approved for their usage in the treatment of vaginal infections, include fungicides. It has been difficult to achieve an optimum effective potential in these compounds. They have been found, when used as gels, foams, creams, ovules and tablets, to decompose almost immediately after being inserted in the vaginal cavity, presenting minimum bioadherence to the walls of the vagina. It is believed that this happens due to their miscibility with water and/or the loss of their physical stability at 37° C. (body temperature). Becoming clear then that they exhibit limited effectiveness.

In U.S. Pat. No. 5,536,743, teaches a compound containing buffered metronidazol. However, this compound only treats bacterian vaginosis, for metronidazole is only effective against bacteria, not against fungus.

In U.S. patent applications no. 20030017207 and 20030064103, a compound containing an azole antifungal agent and a buffered active compound are described, as well as a pharmaceutically acceptable vehicle. The maintenance of the pH of the compounds of this invention is described as of vital importance herein, which should be kept preferably between approximately 2.5 and 5.5.

The buffering system is selected from the group that consists in gluconodeltalactone, acetic acid, fumaric acid, lactic acid, citric acid, propionic acid, malic acid, succinic acid, gluconic acid, ascorbic acid and tartaric acid. The azole active antifungal ingredient is selected from the group consisting in miconazole nitrate, terconazole, butaconazole, itraconazole, voriconazole, ketoconazole, econazole, tioconazole, fluconazole, posconazole, ravuconazole, clotrimazole and similar. The compound also contains a pharmaceutically acceptable vehicle as well as other components such as water, antioxidants, quelant agents, preservatives, oils, waxes, surfactants, emulsifiers, viscosity agents, solvents, mixing agents, solubilizers, bio-adhesives, muco-adhesives and similar agents.

In both documents, the amounts of said components to be used in the compound are clearly described, depending on the nature and consistency of the compound, which can be creams, ointments, ovules, gelified capsules, anhydride polymeric ovules of intravaginal application.

Hence, from the description of the abovementioned documents, it is drawn that the doses of the anti-fungic agent in the treatment of vaginal infections depends on the active ingredient used and its power. In these same documents, a therapeutically effective amount has been defined, given by the dosage found as preferable.

Another problem detected from the analysis of the state of the art, is the need to decrease the term of the treatment and find a form of application less uncomfortable and more effective for the population, in this sense, an attempt to solve this situation is found in the patent application MX No. 02/07641, codependent application to the present one, a fluconazole-and tinidazole pharmaceutical combination is described, its main feature being that the doses used are 150 mg fluconazole and 29 tinidazole for the treatment of infectious diseases in the female reproductive system.

Another case is the patent MX 188,752, wherein a therapeutic method for the treatment of vaginal infections is described and which includes using a combination of itraconazole-secnidazole. The treatment described in this patent is quite lengthy and demands taking 12 doses during the treatment for 3 days, which makes the fulfillment of the treatment by the patient questionable. Recovery is estimated at 77.77%.

Notwithstanding, and following the same research path, in the current investigation, it was amazingly found that the association of fluconazole and tinidazole in lower doses to those known, and administered in only one day of treatment in one or two events, for oral application, was discovered to improve in all aspects over the known treatments for mixed infections in the human reproductive system a feature that represents an edge over other lengthier treatments as it ensures that the patient will follow the treatment much more closely.

Contrary to expectations, diminishing significantly the dose did not affect the effectiveness of the fluconazole-tinidazole association, which held, therefore abating the secondary effects of these substances while keeping their effectiveness.

Another advantage the treatment has is that it is very useful for the medical personnel and communities that, due to various factors, can only access to a clinical diagnostic.

The composition is also effective in the prevention of such infections and provides a safe, effective, economical and provide effective relief from mixed infections in the human reproductive apparatus.

The compound is also effective in preventing such infections and provides a safe, efficient, economical relief of mixed infections in the human reproductive apparatus.

A further advantage is the higher possibility of therapeutic success, allowing for a quick lessening of the symptoms, with a good level of tolerance and acceptance from the part of the patient.

Objectives of the Invention

One of the objects of the present invention is to provide effective relief from mixed infections in the human reproductive apparatus by means of the use of a fluconazole-tinidazole association in lower doses than those already described in the state-of-the-art.

Another object is to cure this kind of infection quickly and efficaciously.

Still another objective of the present invention is to have the patients' total acceptance since it is an only dose.

A further objective is to avoid the patient abandoning the treatment as it takes only one day.

An additional aim is to prevent the development of complications in the upper genital tract.

And, still a further aim is to provide a compound using the fluconazole-tinidazole association for the treatment of infectious diseases in the human reproductive system, which will improve over the traditionally known treatments.

Another object of current invention is to provide a treatment with lower dosages of the principle active agents, which is reflected in a lower incidence of the adverse effects and more benefits to the health of the patient.

DETAILED DESCRIPTION OF THE INVENTION

The present invention is related to the treatment of infectious diseases in the human reproductive system, masculine and feminine by means of the use of a composition which consists of an association of two chemical substances: fluconazole and tinidazole, used in lower doses to those known. Such a combination has proven to be highly efficacious.

The composition of the present invention is administered in one and up to two events, which represents a really important advantage over longer treatments since the patients' acceptance is higher. This, in turn, ensures the patients' following the treatment to its completion.

Fluconazole is a triasolic-derived substance with a wide antimycotic effect; its fusion point is between 138 and 140° C. Its molecular polarity allows for a systemic action both when it is taken orally or parenterally.

Insofar as the pharmacokinetics of fluconazole, this substance is well absorbed, showing total bioavailability of over 90% and, in general, is not affected by medication that modifies the gastrointestinal pH. Neither is its absorbance affected by food ingestion. Furthermore, it distributes itself all over the organism. Due to a low union with plasmatic proteins, the vagina has shown a very smooth distribution of this medication, as the relationship between plasma and the vaginal tissue after oral administration is of 0.94 to 1.1, (which indicates that the concentrations are practically similar) while in vaginal flow, the relationship is 0.5 to 1.0 in respect to plasma and it has proven to be highly effective in the treatment of vaginal candidiasis. In an epidemiological survey, conducted in 1,017 patients suffering from vaginal candidiasis and who were given one dose of 150 mg, fluconazole was well received and effective in 91% of the patients. The appearance of adverse side effects was less than 1%.

Its widespread distribution both in the body tissues and liquids, as well as its 25 to 30 hours life span may account for its effectiveness, both in the short and in the long run. Its prolonged elimination life also contributes to its efficacy.

Tinidazole is a 5-nitroimidazole derivate with selective activity against anaerobes bacteria and protozoan. Tinidazole is totally absorbed orally and spreads throughout the organism. It has a low attachment to proteins, it being 12%. The active mechanism is similar to that of nitroimidazole derivates that produce a bactericidal effect by means of forming toxic metabolites, which brings about the rupture of DNA. The same as other antibiotics that inhibit protein synthesis or affect nucleic acids, nitroimidazole has a post antibiotic effect. Clinical research has shown that tinidazole is effective in the treatment of respiratory infections, intra-abdominal sepsis, amoeba infection, giardasis and gynecological infections produced by *Trichomona vaginallis*. In the treatment of Bacterial Vaginosis, to which *Gardnerella vaginallis* is often associated, using an only doses of 2g tinidazole, yielded a curative rate of 92%, and other researchers using the same amount in a two-day scheme have reported rates of 51%.

Secnidazole is endowed with an anti-parasitical activity and acts against *Entamoeba histolytica, Giardia lamblia, Trichomona vaginallis* and *Gardnerella vaginallis*. After the oral administration of one 2 g dose of secnidazole, the highest seric rates are obtained on the third hour. Average plasmatic life is of about 25 hours. Elimination, essentially urinary, is slow (50% of the doses taken is excreted in 120 hours).

The present composition which comprises an association of two chemical products, as the active principle, in lower doses to the ones commonly known for the treatment of vaginal infections by its activity spectrum, allows for the treatment both of the vaginitis caused by *Candida* sp and *Trichomona vaginallis*, as the one caused by *Gardnerella* and anaerobes bacteria.

Due to the proportions used in the new fluconazole-tinidazole composition, a similar or higher inhibition of the microorganisms which cause mixed vaginal infections as regards the conventional treatments and the dose usually known are obtained.

In the present invention, the composition comprises a fluconazole-tinidazole combination. The weight relationship is from 50 to less than 150 mg of fluconazole and from 1000 to less than 2000 mg of tinidazole. In a preferred embodiment the weight proportion is 112.5 fluconazole to 1500 mg tinidazole. These last values mean diminishing fluconazol from 150 mg to 112,5 mg, that is, 25% less and 2000 mg to 1500 mg, that is, a 25% lower dose than that reported in the published works.

A skilled in the art could expect nothing but a lowering of the therapeutic effect of the medication when the dose is lowered in the amount mentioned, which, as will be shown, does not happen.

The pharmaceutical composition for the treatment of vaginal infections in the present invention, is better taken orally in a wide variety of pharmacy presentations such as Capsules, tablets, pills, effervescent tablets and sublingual tablets, not being limitative in any of them.

In a preferred, but not limitative fashion, the tablets used for the treatment of mixed vaginal infections comprise the fluconazole-tinidazole association in a dose lower to those therapeutically known to date and at least one pharmaceutically acceptable vehicle. Secnidazole is considered to be an alternative ingredient to tinidazole.

Among the pharmaceutically acceptable vehicles we can count, not limiting ourselves to silicon oxide, varieties of glycolate, crospovidone, sodium PVP lauril sulfate, magnesium stearate, isopropyl alcohol.

As regards the preparation of the capsules or tablets for the treatment of mixed vaginal infections, they require an unconventional manufacturing process, given the unusual fluconazole-tinidazole proportion. In order to obtain an excellent uniformity in the product, the process must be controlled. The integration of the fluconazole-tinidazole substances is carried out by making an agglutinating solution, including the chemical product in a lower proportion and that subsequently is used as the granulating solution, wherein the substance with the lower proportion is fluconazole-tinidazole; tinidazole as well as the other components are mixed in a fluid bed to which the agglutinating solution is added to obtain the granular form. The steps subsequent to this one, are the ones commonly used in the making of tablets: drying, grinding and compressing.

The following examples are meant to illustrate this invention, the same not being limitative.

EXAMPLES OF COMPOSITION

Example 1

A pharmaceutical composition including a fluconazole-tinidazole association in the form of tablets is prepared according to the following composition:

| Ingredient | Quantity | % by weight |
|---|---|---|
| Tinidazole | 500 mg | 75% |
| Fluconazole | 37.5 mg | 5.7% |
| Microcrystalline Cellulose 101 | 60.50 mg | 9.2% |
| Sodium glycolate of starch | 6.50 mg | 0.98% |
| Crospovidone | 16.25 mg | 2.4% |
| Lauril sodium sulfate | 6.50 mg | 0.98% |
| Polyvinylpirrolidone K-30 | 19.5 mg | 3.0% |
| Magnesium stearate | 3.25 mg | 0.49% |
| White Opadry YS 7322 | 10.5 mg | 1.6% |
| Total | 660.5 mg | |

Example 2

A pharmaceutical composition including a fluconazole-tinidazole association in the form of tablets is prepared according to the following composition:

| Ingredient | Quantity | % by weight |
|---|---|---|
| Tinidazole | 750 mg | 75% |
| Fluconazole | 56.25 mg | 5.7% |
| Microcrystalline Cellulose 101 | 90.75 mg | 9.2% |
| Sodium glycolate of starch | 9.75 mg | 0.98% |
| Crospovidone | 24.37 mg | 2.5% |
| Lauril sodium sulfate | 9.75 mg | 0.98% |
| Polyvinylpyrrolidone K-30 | 29.25 mg | 3.0% |
| Magnesium stearate | 4.87 mg | 0.49% |
| White Opadry YS 7322 | 15.75 mg | 1.6% |
| Total | 1321 mg | |

Example 3

A pharmaceutical composition including a fluconazole-tinidazole association in the form of tablet is prepared according to the following composition:

| Ingredient | Quantity | % by weight |
|---|---|---|
| Tinidazole | 1500 mg | 75% |
| Fluconazole | 112.5 mg | 5.7% |
| Microcrystalline Cellulose 101 | 181.5 mg | 9.2% |
| Sodium glycolate of starch | 18.15 mg | 0.92% |
| Crospovidone | 48.75 mg | 2.5% |
| Lauril sodium sulfate | 19.5 mg | 0.98% |
| Polyvinylpyrrolidone K-30 | 58.5 mg | 3.0% |
| Magnesium stearate | 9.75 mg | 0.49% |
| White Opadry YS 7322 | 31.5 mg | 1.6% |
| Total | 1981.5 mg | |

Example 4

A pharmaceutical composition including a fluconazole-Secnidazole association in the form of tablets is prepared according to the following composition:

| Ingredient | Quantity | % by weight |
|---|---|---|
| Secnidazole | 500 mg | 75% |
| Fluconazole | 37.5 mg | 5.7% |
| Microcrytalline Cellulose 101 | 60.50 mg | 9.2% |
| Sodium glycolate of starch | 6.50 mg | 0.98% |
| Crospovidone | 16.25 mg | 2.5% |
| Lauril sodium sulfate | 6.50 mg | 0.98% |
| Polyvinylpyrrolidone K-30 | 19.5 mg | 3.0% |
| Magnesium stearate | 3.25 mg | 0.49% |
| White Opadry YS 7322 | 10.5 mg | 1.6% |
| Total | 660.5 mg | |

Pharmacological Examples

A longitudinal study, comparative with a simple random assignation was conducted. The study included 42 females over 18 years old, not pregnant, who showed signs of vaginal infections.

The patients were divided into two groups; Group 1 was given one 150 mg dose of fluconazole and a 2 g tinidazole (standard dose), which is that reported in the co-pendant application of the present application. Group 2 was given a 112.5 mg fluconazole 1500 mg tinidazole association; it was the second group, representing the preferred dose in the present application, an evidently lower dose than the one of the state of the art, yielded surprising results. The medication was given to both groups on two events during one day.

All the patients submitted to a gynecological exploration in order to determine the characteristics of vaginal discharge and the accompanying symptoms were recorded. A pre and post treatment vaginal culture was conducted. The patients were asked to refrain from sexual intercourse in the interval between the taking of the vaginal cultures.

The initial symptoms evaluated were: odor, itching, vulva irritation, dyspareunia and vaginal secretion, which decreased significantly after the treatment.

The results of the initial culture are shown in the following table:

| Infection | No of cases |
|---|---|
| *Gardnerella Vaginalis* | 29 |
| *Gardnerella* and *Actinomyces* | 1 |
| *Gardnerella* and *Candida* | 3 |
| *Gardnerella* and *Micrococcus* | 1 |

-continued

| Infection | No of cases |
|---|---|
| Bacterial Vaginosis | 2 |
| B. Vaginosis and yeast | 1 |
| B. Vaginosis and *Proteus* | 1 |
| B. Vaginosis and *micrococcus* | 1 |
| B. Vaginosis and *E. Coli* | 1 |
| Trichomonas Vaqinalis | 1 |
| Trichomonas | 1 |
| V. + *Gardnerella* + *E. Coli* |   |
| Total number of cases | 2 |

The response to the treatment was as follows:

In the group which was given the standard dose, microbiological eradication was of 82%, while in the group that took the lower dose (i.e. the dose of present application) eradication was of 80%, which showed that, statistically, there is no significant difference between both groups.

TABLE 2

Comparing efficacy of treatments:

| Eradicating germs sensitive to Tx | Treatments | | Total | P. value |
|---|---|---|---|---|
|  | Inventive dose | Standard dose |  |  |
| Yes | 16 (80%) | 18 (82%) | 34 | 0.8690 |
| No | 4 (20%) | 4 (18%) | 8 |  |
| Total | 20 (100%) | 22 (100%) | 42 |  |

As regards adverse effects, only one patient reported to having suffered dizziness and 3 complained from episgastralgia, all of which were temporary.

The fuconazole-tinidazole combination showed to be effective in the treatment of the most commonly found germs in clinical practice of infections in the reproductive system, both in the standard and in the low dose, the adverse effects not having been regarded as important. This is because the minimum inhibiting concentrations of this composition makes it possible to reach an eradication percentage similar to the eradication percentages already usually obtained by 150 mg fluconazole and 2.0 g tinidazole With the present invention it was unexpectedly found that, in doses lower to those already known of the fluconazole-tinidazole chemical compounds, the same therapeutic effects were achieved but with fewer adverse effects.

It is believed that Applicant's invention includes many other embodiments which are not herein specifically described accordingly this disclosure should not be read as being limited to the foregoing examples or preferred embodiments.

We claim:

1. A pharmaceutical composition for oral administration, wherein said composition comprises from about 100 to less than about 112.5 mg of fluconazole and from about 1000 to less than about 1500 mg of tinidazole.

2. The pharmaceutical composition according to claim 1, wherein the composition further comprises a vehicle mixture of acceptable pharmaceutical vehicles that comprises microcrystalline cellulose, sodium glycolate of starch, polyvinylpyrrolidone, magnesium stearate and white opadry.

3. The pharmaceutical composition according to claim 2, wherein the composition is in tablet form.

* * * * *